US012766081B2

(12) United States Patent
Nashte et al.

(10) Patent No.: US 12,766,081 B2
(45) Date of Patent: Oct. 20, 2026

(54) PERSONAL CARE COMPOSITION

(71) Applicant: FINE ORGANIC INDUSTRIES LIMITED, Mumbai (IN)

(72) Inventors: Subhash Shivaling Nashte, Mumbai (IN); Shriniwas Machhindranath Sawant, Mumbai (IN)

(73) Assignee: FINE ORGANIC INDUSTRIES LIMITED, Mumbai (IN)

( * ) Notice: Subject to any disclaimer, the term of this patent is extended or adjusted under 35 U.S.C. 154(b) by 296 days.

(21) Appl. No.: 18/281,925

(22) PCT Filed: Mar. 16, 2022

(86) PCT No.: PCT/IN2022/050251
§ 371 (c)(1),
(2) Date: Sep. 13, 2023

(87) PCT Pub. No.: WO2022/195624
PCT Pub. Date: Sep. 22, 2022

(65) Prior Publication Data

US 2024/0165000 A1 May 23, 2024

(30) Foreign Application Priority Data

Mar. 18, 2021 (IN) ............................ 202121011541

(51) Int. Cl.

| | |
|---|---|
| ***A61K 8/37*** | (2006.01) |
| ***A23K 20/158*** | (2016.01) |
| ***A23K 50/75*** | (2016.01) |
| ***A61Q 17/00*** | (2006.01) |

(52) U.S. Cl.
CPC .............. *A61K 8/37* (2013.01); *A23K 20/158* (2016.05); *A23K 50/75* (2016.05); *A61Q 17/005* (2013.01); *A61K 2800/30* (2013.01); *A61K 2800/74* (2013.01)

(58) Field of Classification Search
CPC .. A61K 8/37; A61K 2800/30; A61K 2800/74; A61K 8/375; A23K 20/158; A23K 50/75; A23K 50/70; A61Q 17/005; A61Q 5/02; A61Q 19/00; A61Q 19/10; A23V 2002/00; C11D 3/48; C11D 3/2093
See application file for complete search history.

(56) References Cited

U.S. PATENT DOCUMENTS

| | | | |
|---|---|---|---|
| 2011/0305646 | A1 | 12/2011 | Lenn et al. |
| 2018/0325791 | A1 * | 11/2018 | Lane et al. |

FOREIGN PATENT DOCUMENTS

| | | | | |
|---|---|---|---|---|
| DE | 2338462 | A1 | | 2/1975 |
| EP | 0465423 | A2 | | 1/1992 |
| WO | WO2020046879 | A1 | * | 3/2020 |
| WO | WO2020147953 | A1 | * | 7/2020 |
| WO | 2020/182288 | A1 | | 9/2020 |
| WO | WO2020182288 | | * | 9/2020 |
| WO | 2021/052856 | A1 | | 3/2021 |

OTHER PUBLICATIONS

International Search Report and Written Opinion issued by the International Searching Authority in corresponding International Application No. PCT/IN2022/050251 mailed Jul. 20, 2022.

* cited by examiner

*Primary Examiner* — Robert A Wax
*Assistant Examiner* — Kimberly Barber
(74) *Attorney, Agent, or Firm* — ArentFox Schiff LLP

(57) ABSTRACT

A glycerol ester mixture comprising at least 30% monoglyceride useful in the preparation of personal care composition and nutritional feed for birds; wherein the glycerol ester mixture is prepared by reacting glycerol with a fatty acid mixture of caprylic acid and capric acid in weight ratio of 30:70 to 70:30.

17 Claims, No Drawings

PERSONAL CARE COMPOSITION

CROSS-REFERENCE TO RELATED APPLICATIONS

This application is a National Stage Entry of International Application No. PCT/IN2022/050251, filed Mar. 16, 2022, which claims priority to Indian Patent Application No. 202121011541, filed Mar. 18, 2021. The disclosures of the priority documents are incorporated in their entireties by reference herein.

The present invention relates to a personal care composition comprising glycerol ester mixture effective against microbes.

BACKGROUND OF THE INVENTION

German Patent number DE2338462 (assigned to Chemische Fabrik Gronau GmbH) teaches a combination of 0.2-0.3% RCO2CH2CH(OH)CH2OR1 (I where R=straight chain C5-7 and R1=H, Ac, or EtCO) with 0.1-0.5% of methyl and/or ethyl p-hydroxybenzoate showed synergistic effect if used for preservation of cosmetics, pharmaceuticals and food. The personal care composition with glycerol ester mixture of the present invention comprises RCO2CH2CH(OH)CH2OR1 wherein R, R1=$C_8$, $C_{10}$.

United States Publication number 20110305646 (applicant Lenn etal) discloses monoglycerides with capric acid or lauric acid or undecanoic acid as the fatty acid useful in treating fungal conditions caused by *T. rubrum*. The present invention comprises personal care compositions of glycerol ester mixture from capric acid and caprylic acid useful as preservative and/or as an emulsifier.

European Patent number 465423 teaches pharmaceutical compositions for killing microorganisms comprising $C_4$ to $C_{22}$ fatty acids and monoglycerides thereof. The present invention comprises personal care compositions of glycerol ester mixture from capric acid and caprylic acid useful as preservative and/or as an emulsifier.

OBJECT OF THE INVENTION

The object of the present invention is to provide a personal care composition with a glycerol ester mixture, its process of preparation and use in shampoo, lotions, creams, veggie wash, different personal care preparation, scalp cleanser, hair cleanser, shower preparations, shower gels, foam baths, gels, body wash, facial cleanser, face wash, makeup remover, cleansing wipe, sunscreen, foundation and the like.

Another object of the present invention is to provide a personal care composition of glycerol ester mixture which is free of preservative.

Yet another object of the present invention is to provide a personal care composition of glycerol ester mixture free of preservative, sulfate, ethylene oxide, amide and silicone.

SUMMARY OF THE INVENTION

A personal care composition comprising a. 0.5 to 10 weight % of glycerol ester mixture comprising at least 30% monoglyceride wherein the weight % is on the weight of the composition and b. one or more excipients;

wherein the glycerol ester mixture is prepared by reacting glycerol with a fatty acid mixture of caprylic acid and capric acid in weight ratio of 30:70 to 70:30.

A personal care composition comprising a. 0.5 to 10 weight % of glycerol pelargonic ester comprising at least 30% monoglyceride wherein the weight % is on the weight of the composition and b. one or more excipients.

DESCRIPTION OF THE INVENTION

Personal care compositions with mild preservatives are in demand by consumers.

It is known that sulfates in personal care compositions may damage cells and strip away natural oils and hair proteins & ethanolamide based surfactants may comprise nitroso compounds which are considered harmful when in contact with skin.

In view of the same we have developed a personal care composition which is stable and mild. The personal care composition of the present invention is user friendly as it is preservative free, sulfate free, amide free, ethylene oxide free, silicone free, paraben free and formaldehyde free.

According to one embodiment of the present invention is a personal care composition comprising glycerol ester mixture comprising at least 30% monoglyceride, and one or more excipients. The glycerol ester mixture is prepared by esterification of fatty acid mixture of caprylic acid and capric acid in weight ratio of 30:70 to 70:30.

The personal care composition comprises glycerol ester mixture in 0.5 to 10 weight %. The weight % used herein is on the weight of the composition.

The excipients used in the personal care composition of the present invention are selected from anionic, cationic, zwiterrionic, nonionic, amphoteric surfactants; superfatting agents, stabilizers, biogenic active ingredients, humectants, preservatives, pearlizing agents, dyes and pigments, fragrances, solvents, opacifiers, further thickeners and dispersants, protein derivatives such as gelatin, collagen hydrolysates, polypeptides, fatty alcohols, odor masking agents and enzymes.

The glycerol ester mixture used herein is characterized by hydroxyl value less than 400.

The glycerol ester mixture used herein is characterized by dropping point is less than −10° C.

The glycerol ester mixture used herein is characterized by acid value is less than 2.0.

The glycerol ester mixture used herein is characterized by saponification value is less than 300.

The glycerol ester mixture used herein is characterized by iodine value is less than 1.

The glycerol ester mixture used in the personal care composition of the present invention is effective against microbes thereby eliminating the need of a preservative.

The glycerol ester mixture is effective against microbes selected from *Staphylococcus aureus, Bacillus subtilis, E. Coli, Pseudomonas aeruginosa, Salmonella enteric, Propionebacterium acne, Malassezia furfur, Streptococcus mutans, Lactobacillis acidophilus, Candida albicans, Aspergillus niger* and the like.

The personal care composition of the present invention is free of preservatives.

The glycerol ester mixture used in the personal care composition of the present invention emulsifies upto 50% oil by weight thereby eliminating the need of a sulfate-based emulsifier.

The personal care composition of the present invention is free of sulfate-based emulsifiers.

The personal care composition of the present invention is selected from shampoo, lotions, creams, veggie wash, different personal care preparation scalp cleanser, lotions, creams, veggie wash, different personal care preparation, hair cleanser, shower preparations, shower gels, foam baths, gels, body wash, facial cleanser, face wash, makeup remover, cleansing wipe, sunscreen, foundation and the like.

The glycerol ester mixture used in the present invention is normally prepared by reacting glycerol with caprylic and capric acids at 100 to 200° C. with continuous removal of water. Once the reaction is complete, any residual fatty acid is stripped by distillation and excess glycerol is separated by gravity and/or washing or stripped by other means such as distillation.

According to another embodiment of the present invention is a feed nutritional composition comprising glycerol ester mixture comprising at least 30% monoglyceride, which can be mixed with poultry feed. The glycerol ester mixture is prepared by esterification of fatty acid mixture of caprylic acid and capric acid in weight ratio of 30:70 to 70:30.

We have found that the glycerol ester mixture can be administered with poultry feed and protects poultry from low pathogenic (LPAI) and highly pathogenic (HPAI) infections.

According to yet another embodiment of the present invention is a personal care composition comprising glycerol pelargonic ester comprising at least 30% monoglyceride, and one or more excipients.

The personal care composition comprises glycerol pelargonic ester in 0.5 to 10 weights %. The weight % used herein is on the weight of the composition.

The excipients used in the personal care composition of the present invention are selected from anionic, cationic, zwiterrionic, nonionic, amphoteric surfactants; superfatting agents, stabilizers, biogenic active ingredients, humectants, preservatives, pearlizing agents, dyes and pigments, fragrances, solvents, opacifiers, further thickeners and dispersants, protein derivatives such as gelatin, collagen hydrolysates, polypeptides, fatty alcohols, odor masking agents and enzymes.

The glycerol pelargonic ester used herein is characterized by hydroxyl value less than 400.

The glycerol pelargonic ester used herein is characterized by dropping point less than −10° C.

The glycerol pelargonic ester used herein is characterized by acid value less than 2.0.

The glycerol pelargonic ester used herein is characterized by saponification value less than 300.

The glycerol pelargonic ester used herein is characterized by iodine value less than 1.

The glycerol pelargonic ester used in the personal care composition of the present invention is effective against microbes thereby eliminating the need of a preservative.

The glycerol pelargonic ester is effective against microbes selected from *Staphylococcus aureus, Bacillus subtilis, E. Coli, Pseudomonas aeruginosa, Salmonella enteric, Propionebacterium acne, Malassezia furfur, Streptococcus mutans, Lactobacillis acidophilus, Candida albicans, Aspergillus niger* and the like.

The personal care composition of the present invention is free of preservatives.

The glycerol pelargonic ester used in the personal care composition of the present invention emulsifies upto 50% oil by weight thereby eliminating the need of a sulfate based emulsifier.

The personal care composition of the present invention is free of sulfate based emulsifiers.

The personal care composition of the present invention is selected from shampoo, lotions, creams, veggie wash, different personal care preparation scalp cleanser, lotions, creams, veggie wash, different personal care preparation, hair cleanser, shower preparations, shower gels, foam baths, gels, body wash, facial cleanser, face wash, makeup remover, cleansing wipe, sunscreen, foundation and the like.

The glycerol pelargonic ester used in the present invention is normally prepared by reacting glycerol with pelargonic acid at 100 to 200° C. with continuous removal of water. Once the reaction is complete, any residual pelargonic acid is stripped by distillation and excess glycerol is separated by gravity and/or washing or stripped by other means such as distillation.

Definition of Terms

Dropping Point

The dropping point is the temperature at which a substance passes from a semi-solid to a liquid state.

Pour Point

The pour point of a liquid is the lowest temperature at which it becomes semi solid. This is where the liquid loses its flow characteristics.

Acid Value

Acid value (or neutralization number or acid number or acidity) is the mass of potassium hydroxide (KOH) in milligrams that is required to neutralize one gram of chemical substance. The acid number is a measure of the number of carboxylic acid groups in a chemical compound, such as a fatty acid.

Saponification Value

Saponification value or saponification number (SV or SN) represents the number of milligrams of potassium hydroxide (KOH) required to saponify one gram of fat under the conditions specified.

Hydroxyl Value

The hydroxyl value of a substance is the amount, in milligrams, of potassium hydroxide required to neutralize any acid when combined by acylation in 1 g of the substance under examination.

Iodine Value

The iodine value (or iodine adsorption value or iodine number or iodine index, commonly abbreviated as IV) is the mass of iodine in grams that is consumed by 100 grams of a chemical substance. Iodine value is used to determine the amount of unsaturation in fats, oils and waxes.

The following examples illustrate preferred embodiments in accordance with the present invention without limiting the scope of the invention.

EXAMPLES

Finester 6090 is the trade name for glycerol ester mixture comprising at least 30% monoglyceride prepared by known methods such as reacting glycerol with caprylic and capric acids at 100 to 200° C. with continuous removal of water. Once the reaction is complete, any residual fatty acid is stripped by distillation and excess glycerol is separated by gravity and/or washing or stripped by other means such as distillation.

The esterified mixture of the present invention, Finester 6090, is used for the examples 1 and 2 below.

Typical characteristic values of Finester 6090 are as follows—

| Sr. No. | Particulars | Finester 6090 |
|---|---|---|
| 1 | Dropping Point | <−10 °C |
| 2 | Acid Value | 2.0 Max |
| 3 | Sap Value | 252 |
| 4 | Hydroxyl Value | 370 |
| 5 | Iodine Value | <1 |

Test Methods Used

Dropping Point: D 566-02

Acid Value: A.O.C.S. Cd 3d-63 (09)

Saponification Value: A.O.C.S. Cd 3-25(09)

Hydroxyl Value: A.O.C.S. Cd 13-60 (16)

Iodine Value: A.O.C.S. Tg 1a-64 (09)

Example 1: KL6-39 Series

| Personal Care Composition for Challenge Testing | |
|---|---|
| KL6-39 Series | 1<br>% (w/w) |
| Deionized Water | 74.30 |
| Keltrol CG-T | 0.30 |
| Finester 2009 | 2.00 |
| Safflower Oil | 5.00 |
| Jojoba Oil | 5.00 |
| Protachem CTG | 10.00 |
| Finester 6090 | 3.00 |
| Citric Acid | 0.1 |
| Trisodium Citrate | 0.3 |
| Totals | 100.00 |

Example 2: KL6-33 Series

| Personal Care Composition for Challenge Testing | | | | | | | | |
|---|---|---|---|---|---|---|---|---|
| | KL6-33 Series | | | | | | | |
| | 1<br>% (w/w) | 2<br>% (w/w) | 3<br>% (w/w) | 4<br>% (w/w) | 5<br>% (w/w) | 6<br>% (w/w) | 7<br>% (w/w) | 8<br>% (w/w) |
| Deionized Water | 99.40 | 98.90 | 98.40 | 97.70 | 97.20 | 96.20 | 95.20 | 96.20 |
| KL6-31/2 | x | x | x | x | x | x | x | x |
| Pemulen TR-2 | 0.30 | 0.30 | 0.30 | 0.30 | 0.30 | 0.30 | 0.30 | 0.30 |
| Potassium Hydroxide | 0.30 | 0.30 | 0.30 | 0.30 | 0.30 | 0.30 | 0.30 | 0.30 |
| Finester 2009 | x | x | x | x | x | 1.00 | 2.00 | 3.00 |
| Finester 6090 | x | 0.50 | 1.00 | 1.50 | 2.00 | 2.00 | 2.00 | x |
| Citric Acid | | | | 0.20 | 0.20 | 0.20 | 0.20 | 0.20 |
| Totals | 100.00 | 100.00 | 100.00 | 100.00 | 100.00 | 100.00 | 100.00 | 100.00 |

Example 3: Microbial Testing

| Product Name | Efficacy against Bacteria | MIC % | Applications |
|---|---|---|---|
| Finester 6090 | *Staphylococcus aureus* | 0.05% | Feed/Nutritional Supplement/Personal Care/Pharma applications |
| | *Bacillus subtilis* | 0.1% | |
| | *E. Coli* | >1.0% | |
| | *Pseudomonas aeruginosa* | >1.0% | |
| | *Salmonella enterica* | 0.5% | |
| | Propionebacterium acne | 1.0% | |
| | *Malassezia furfur* | 1.0% | |
| | *Streptococcus mutans* | 0.08% | |
| | *Lactobacillis acidophilus* | 0.1% | |
| | *Candida albicans* | 0.5% | |

Challenge Test Method: Antimicrobial Preservative Effectiveness (APE) Testing CTFA Materials:

a) Microorganisms listed in the table below:

| Organism | ATCC NO |
|---|---|
| *Staphylococcus aureus* | ATCC 6538 |
| *Escherichia coli* | ATCC 8739 |
| *Pseudomonas aeruginosa* | ATCC 9027 |
| *Candida albicans* | ATCC 10231 |
| *Aspergillus niger* | ATCC 14404 |

b) Letheen agar, SDA agar, or other agar containing compounds capable of binding preservatives in the plated sample.

c) Sterile petri dishes d) Sterile pipettes e) Sterile diluent-DE broth, 0.9% saline with or without Tween 80 f) Routine microbiological test material for doing plate count determination.

Procedure:

Validation of Microbial Recovery (Neutralizer)

This step evaluates the suitability of neutralizer used for the APE test.

The above organisms are inoculated in three different test tubes (replicates)

a) Inoculate less than 100 cfu of each organism into the product and dilute in DE broth (neutralizer) in 3 replicates of petri plates.

b) Inoculate less than 100 cfu of each organism without the product and dilute in DE broth in 3 replicates of petri plates Place 1 ml of each dilution onto each sterile petri dish.

Pour Letheen agar on the set used with bacterial culture and pour SDA agar on the set used with fungal culture. About 12-15 ml of agar should be poured onto the plates.

Gently swirl plates. Allow the agar to solidify.

Incubate all plates' inverted position with Letheen agar at 30-35° C. for 72 hours.

Incubate SDA plate for 5-7 days at 20-25° C.

Examine for growth and record results.

The five organisms should show growth which validates the suitability of the test.

On Day 0:

Inoculate 1 ml of each culture (mentioned in the table) in 20 g/20 ml of product to be tested in a sterile cup. (Note: DO NOT DISCARD THIS SAMPLE. YOU WILL NEED IT THROUGH THE WHOLE PERIOD OF TESTING);

For Control preparation inoculate 1 ml of each culture in 20 ml of sterile saline.

Obtain the rack(s) of 9 ml saline diluent to be used.

Carry out diluent calibration for eight randomly selected saline tubes from the rack (s).

Now dilute product using de broth folLowed by saline until the final dilution reaches $1\times10^6$ CFU. (Note: De broth is must for dilution of product.)

Dilute control using saline only until the final dilution reaches $1\times10^6$ CFU.

Plate I ml of each dilution onto each sterile petri dish.

Pour Letheen agar on the set used with bacterial culture and pour SDA agar on the set used with fungal culture. About 12-15 ml of agar should be poured onto the plates.

Gently swirl plates. Allow the agar to solidify.

Incubate all plates' inverted position with Letheen agar at 30-35° C. for 72 hours.

Incubate SDA plate for 5-7 days at 20-25° C.

Record the results of day 0 plates after 7 days in the raw data book.

On Day 7, Day 14, Day 21 and Day 28:

Obtain the original sterile cup (20 g sample+organism) made on day 0.

Use this sample & follow the same procedure as DAY 0 for calibration of diluent, dilution and plating.

Population Monitoring

On days 7, 14, 21, and 28 monitor the growth on the plates and record the data.

NOTE: If the preservative is working the population should decrease with days. The preservative is ineffective if there is no change in growth.

Calculation:

Assume control growth as 100% then calculate sample growth of each organism percentile.

Special Applications:

This section is reserved for adding to the general procedure variations as may be required from time to time to accurately test a sample.

Topical creams (water in oil or oil in water emulsions); the saline dilution blanks must contain Tween 80 at 1% minimal.

For Re-challenge testing redo the whole procedure by inoculating all the fresh cultures in same previous sample cups.

Challenge Test LOT#KL6-39/1

| | CONTROL GROWTH | SAMPLE GROWTH | % DE-CREASE | INNOC-ULUM LEVEL |
|---|---|---|---|---|
| DAY 0 | | | | |
| *Escherichia Coli* | 199^5 | 79^5 | 60.30% | OK |
| *Staphylococcus Aureus* | 108^5 | 98^5 | 9.26% | OK |
| *Pseudomonas Aeruginosa* | 197^5 | 78^5 | 60.41% | OK |
| *Candida Albicans* | 55^5 | 32^5 | 41.82% | OK |
| *Aspergillus Niger* | 60^5 | 22^% | 63.33% | OK |
| DAY 7 | | | | |
| *Escherichia Coli* | | 0^2 | >99.99% | |
| *Staphylococcus Aureus* | | 0^2 | >99.99% | |
| *Pseudomonas Aeruginosa* | | 0^2 | >99.99% | |
| *Candida Albicans* | | 0^2 | >99.99% | |
| *Aspergillus Niger* | | 0^2 | >99.99% | |
| DAY 14 | | | | |
| *Escherichia Coli* | | <1^2 | 99.90% | |
| *Staphylococcus Aureus* | | <1^2 | >99.9% | |
| *Pseudomonas Aeruginosa* | | <1^2 | >99.9% | |
| *Candida Albicans* | | <1^2 | 99.90% | |
| *Aspergillus Niger* | | <15^2 | 99.99% | |
| DAY 21 | | | | |
| *Escherichia Coli* | | <1^2 | >'99.9% | |
| *Staphylococcus Aureus* | | <1^2 | >99.99% | |
| *Pseudomonas Aeruginosa* | | <1^2 | >99.99% | |
| *Candida Albicans* | | <1^2 | 100% | |
| *Aspergillus Niger* | | 6^2 | 100% | |
| DAY 28 | | | | |
| *Escherichia Coli* | | <1^2 | >99.99 | |
| *Staphylococcus Aureus* | | <1^2 | >99.9% | |
| *Pseudomonas Aeruginosa* | | <1^2 | >99.9% | |
| *Candida Albicans* | | <1^2 | >99.99 | |
| *Aspergillus Niger* | | <1^2 | >99.99 | |

Challenge Test LOT# KL6-33/4

| | CONTROL GROWTH | SAMPLE GROWTH | % DE-CREASE | INNOC-ULUM LEVEL |
|---|---|---|---|---|
| DAY 0 | | | | |
| *Escherichia Coli* | 199^5 | 100^5 | 49.75% | OK |
| *Staphylococcus Aureus* | 108^5 | 81^5 | 25.00% | OK |
| *Pseudomonas Aeruginosa* | 197^5 | 87^5 | 50.76% | OK |
| *Candida Albicans* | 55^5 | 25^5 | 54.55% | OK |
| *Aspergillus Niger* | 60^5 | 20^% | 66.67% | OK |
| DAY 7 | | | | |
| *Escherichia Coli* | | 10 | >99.99% | |
| *Staphylococcus Aureus* | | 18 | >99.9% | |
| *Pseudomonas Aeruginosa* | | 20 | >99.9% | |
| *Candida Albicans* | | 5 | >99.9% | |
| *Aspergillus Niger* | | 1 | >99.9% | |
| DAY 14 | | | | |
| *Escherichia Coli* | | <1^2 | 99.90% | |
| *Staphylococcus Aureus* | | <1^2 | >99.9% | |
| *Pseudomonas Aeruginosa* | | <1^2 | >99.9% | |
| *Candida Albicans* | | <1^2 | 99.90% | |
| *Aspergillus Niger* | | 1 | 99.99% | |
| DAY 21 | | | | |
| *Escherichia Coli* | | <1^2 | >'99.9% | |
| *Staphylococcus Aureus* | | <1^2 | >99.99% | |
| *Pseudomonas Aeruginosa* | | <1^2 | >99.99% | |
| *Candida Albicans* | | <1^2 | 100% | |
| *Aspergillus Niger* | | 1 | 100% | |

-continued

Challenge Test LOT# KL6-33/4

| | CONTROL GROWTH | SAMPLE GROWTH | % DE-CREASE | INNOC-ULUM LEVEL |
|---|---|---|---|---|
| DAY 28 | | | | |
| *Escherichia Coli* | | <1^2 | >99.99 | |
| *Staphylococcus Aureus* | | <1^2 | >99.9% | |
| *Pseudomonas Aeruginosa* | | <1^2 | >99.9% | |
| *Candida Albicans* | | <1^2 | >99.99 | |
| *Aspergillus Niger* | | <1^2 | >99.99 | |

Challenge Test LOT # KL6-33/5

| | CONTROL GROWTH | SAMPLE GROWTH | % DE-CREASE | INNOC-ULUM LEVEL |
|---|---|---|---|---|
| DAY 0 | | | | |
| *Escherichia Coli* | 199^5 | 90^5 | 54.77% | OK |
| *Staphylococcus Aureus* | 108^5 | 75^5 | 30.56% | OK |
| *Pseudomonas Aeruginosa* | 197^5 | 87^5 | 55.84% | OK |
| *Candida Albicans* | 55^5 | 15^5 | 72.73% | OK |
| *Aspergillus Niger* | 60^5 | 9^5 | 85.00% | OK |
| DAY 7 | | | | |
| *Escherichia Coli* | | <1^2 | >99.99% | |
| *Staphylococcus Aureus* | | <1^2 | >99.9% | |
| *Pseudomonas Aeruginosa* | | <1^2 | >99.9% | |
| *Candida Albicans* | | <1^2 | >99.9% | |
| *Aspergillus Niger* | | <1^2 | >99.9% | |
| DAY 14 | | | | |
| *Escherichia Coli* | | <1^2 | 99.90% | |
| *Staphylococcus Aureus* | | <1^2 | >99.9% | |
| *Pseudomonas Aeruginosa* | | <1^2 | >99.9% | |
| *Candida Albicans* | | <1^2 | 99.90% | |
| *Aspergillus Niger* | | 5^2 | 99.99% | |
| DAY 21 | | | | |
| *Escherichia Coli* | | <1^2 | >'99.9% | |
| *Staphylococcus Aureus* | | <1^2 | >99.99% | |
| *Pseudomonas Aeruginosa* | | <1^2 | >99.99% | |
| *Candida Albicans* | | <1^2 | 100% | |
| *Aspergillus Niger* | | 3^2 | 100% | |
| DAY 28 | | | | |
| *Escherichia Coli* | | <1^2 | >99.99 | |
| *Staphylococcus Aureus* | | <1^2 | >99.9% | |
| *Pseudomonas Aeruginosa* | | <1^2 | >99.9% | |
| *Candida Albicans* | | <1^2 | >99.99 | |
| *Aspergillus Niger* | | <1^2 | >99.99 | |

Challenge Test LOT# KL6-33/6

| | CONTROL GROWTH | SAMPLE GROWTH | % DE-CREASE | INNOC-ULUM LEVEL |
|---|---|---|---|---|
| DAY 0 | | | | |
| *Escherichia Coli* | 199^5 | 90^5 | 54.77% | OK |
| *Staphylococcus Aureus* | 108^5 | 95^5 | 12.04% | OK |
| *Pseudomonas Aeruginosa* | 197^5 | 98^5 | 50.76% | OK |
| *Candida Albicans* | 55^5 | 40^5 | 9.09% | OK |
| *Aspergillus Niger* | 60^5 | 23^5 | 15.00% | OK |
| DAY 7 | | | | |
| *Escherichia Coli* | | <1^2 | >99.99% | |
| *Staphylococcus Aureus* | | <1^2 | >99.9% | |

-continued

Challenge Test LOT# KL6-33/6

| | CONTROL GROWTH | SAMPLE GROWTH | % DE-CREASE | INNOC-ULUM LEVEL |
|---|---|---|---|---|
| *Pseudomonas Aeruginosa* | | <1^2 | >99.9% | |
| Candida Albicans | | <1^2 | >99.9% | |
| *Aspergillus Niger* | | <1^2 | >99.9% | |
| DAY 14 | | | | |
| *Escherichia Coli* | | <1^2 | 99.90% | |
| *Staphylococcus Aureus* | | <1^2 | >99.9% | |
| *Pseudomonas Aeruginosa* | | <1^2 | >99.9% | |
| *Candida Albicans* | | <1^2 | 99.90% | |
| *Aspergillus Niger* | | 4^2 | 99.99% | |
| DAY 21 | | | | |
| *Escherichia Coli* | | <1^2 | >'99.9% | |
| *Staphylococcus Aureus* | | <1^2 | >99.99% | |
| *Pseudomonas Aeruginosa* | | <1^2 | >99.99% | |
| *Candida Albicans* | | <1^2 | 100% | |
| *Aspergillus Niger* | | 3^2 | 100% | |
| DAY 28 | | | | |
| *Escherichia Coli* | | <1^2 | >99.99 | |
| *Staphylococcus Aureus* | | <1^2 | >99.9% | |
| *Pseudomonas Aeruginosa* | | <1^2 | >99.9% | |
| *Candida Albicans* | | <1^2 | >99.99 | |
| *Aspergillus Niger* | | <1^2 | >99.99 | |

Challenge Test LOT# KL6-33/7

| | CONTROL GROWTH | SAMPLE GROWTH | % DE-CREASE | INNOC-ULUM LEVEL |
|---|---|---|---|---|
| DAY 0 | | | | |
| *Escherichia Coli* | 199^5 | 95^5 | 52.26% | OK |
| *Staphylococcus Aureus* | 108^5 | 64^5 | 40.74% | OK |
| *Pseudomonas Aeruginosa* | 197^5 | 89^5 | 54.82% | OK |
| *Candida Albicans* | 55^5 | 20^5 | 63.64% | OK |
| *Aspergillus Niger* | 60^5 | 35^5 | 41.67% | OK |
| DAY 7 | | | | |
| *Escherichia Coli* | | 1^2 | >99.99% | |
| *Staphylococcus Aureus* | | <1^2 | >99.9% | |
| *Pseudomonas Aeruginosa* | | <1^2 | >99.9% | |
| *Candida Albicans* | | 20^2 | >99.9% | |
| *Aspergillus Niger* | | | >99.9% | |
| DAY 14 | | | | |
| *Escherichia Coli* | | <1^2 | 99.99% | |
| *Staphylococcus Aureus* | | <1^2 | >99.9% | |
| *Pseudomonas Aeruginosa* | | <1^2 | >99.9% | |
| *Candida Albicans* | | <1^2 | >99.99% | |
| *Aspergillus Niger* | | <1^2 | >99.99% | |
| DAY 21 | | | | |
| *Escherichia Coli* | | <1^2 | >'99.9% | |
| *Staphylococcus Aureus* | | <1^2 | >99.99% | |
| *Pseudomonas Aeruginosa* | | <1^2 | >99.99% | |
| *Candida Albicans* | | <1^2 | >99.99 | |
| *Aspergillus Niger* | | <1^2 | >99.99 | |
| DAY 28 | | | | |
| *Escherichia Coli* | | <1^2 | >99.99 | |
| *Staphylococcus Aureus* | | <1^2 | >99.99% | |
| *Pseudomonas Aeruginosa* | | <1^2 | >99.9% | |
| *Candida Albicans* | | <1^2 | >99.99 | |
| *Aspergillus Niger* | | <1^2 | >99.99 | |

| Challenge Test LOT # KL6-33/8 | | | | |
|---|---|---|---|---|
| | CONTROL GROWTH | SAMPLE GROWTH | % DE-CREASE | INNOCULUM LEVEL |
| DAY 0 | | | | |
| *Escherichia Coli* | 199^5 | 132^5 | 93.37% | OK |
| *Staphylococcus Aureus* | 108^5 | 90^5 | 16.67% | OK |
| *Pseudomonas Aeruginosa* | 197^5 | 97^5 | 50.76% | OK |
| *Candida Albicans* | 55^5 | 40^5 | 27.27% | OK |
| *Aspergillus Niger* | 60^5 | 30^5 | 60.00% | OK |
| DAY 7 | | | | |
| *Escherichia Coli* | | 100^5 | 49.74% | |
| *Staphylococcus Aureus* | | 80^5 | 25.92% | |
| *Pseudomonas Aeruginosa* | | 50^5 | 74.61% | |
| *Candida Albicans* | | 20^5 | 63.63% | |
| *Aspergillus Niger* | | 3^5 | >99.9% | |
| DAY 14 | | | | |
| *Escherichia Coli* | | 102^5 | FAIL | |
| *Staphylococcus Aureus* | | 95^5 | FAIL | |
| *Pseudomonas Aeruginosa* | | 101^5 | FAIL | |
| *Candida Albicans* | | 31^5 | FAIL | |
| *Aspergillus Niger* | | 50^5 | FAIL | |
| DAY 21 | | | | |
| *Escherichia Coli* | | 105^5 | FAIL | |
| *Staphylococcus Aureus* | | 101^5 | FAIL | |
| *Pseudomonas Aeruginosa* | | 70^5 | FAIL | |
| *Candida Albicans* | | 19^5 | FAIL | |
| *Aspergillus Niger* | | 16^5 | FAIL | |
| DAY 28 | | | | |
| *Escherichia Coli* | | 100^5 | FAIL | |
| *Staphylococcus Aureus* | | 90^5 | FAIL | |
| *Pseudomonas Aeruginosa* | | 69^5 | FAIL | |
| *Candida Albicans* | | 21^5 | FAIL | |
| *Aspergillus Niger* | | 18^2 | FAIL | |

Summary of Microbial Study

Finester 6090 is an effective preservative at levels between 0.5 to 10%.

Example 4: The Evaluation of Finester 6090 as a Feed Nutritional Supplement Against LPAI/HPAI Infections in Poultry Finester 6090 is evaluated as a nutritional feed in one layer farm in Ambala, Punjab, India with total no of birds on the farm approx. 15000 nos.

About 300 gms Finester 6090 was mixed with feed for 1000 birds for 15 days.

| | Mortality Rate |
|---|---|
| Before administration of finester 6090 | Around 400 birds/day |
| Post administration of finester 6090 for 15 days | Around 33 birds/day |

We claim:

1. A personal care composition comprising:

a. 0.5 to 10 weight % of a glycerol ester mixture, wherein the glycerol ester mixture comprises at least 30% monoglyceride, and b. one or more excipients selected from anionic, cationic, zwiterrionic, nonionic, and amphoteric surfactants, superfatting agents, stabilizers, biogenic active ingredients, humectants, preservatives, pearlizing agents, dyes, pigments, fragrances, solvents, opacifiers, thickeners, dispersants, protein derivatives, polypeptides, fatty alcohols, odor masking agents, and enzymes, wherein the glycerol ester mixture is prepared by reacting glycerol with a fatty acid mixture of caprylic acid and capric acid in a weight ratio of 30:70 to 70:30.

2. The personal care composition according to claim 1, wherein the glycerol ester mixture is effective against microbes.

3. The personal care composition according to claim 2, wherein the microbes are selected from *Staphylococcus aureus, Bacillus subtilis, E. coli, Pseudomonas aeruginosa, Salmonella enteric, Propionebacterium acne, Malassezia furfur, Streptococcus mutans, Lactobacillis acidophilus, Candida albicans*, and *Aspergillus niger.*

4. The personal care composition according to in claim 1, the composition comprises no preservative.

5. The personal care composition according to claim 1, wherein the glycerol ester mixture emulsifies up to 50% oil by weight.

6. The personal care composition according to claim 1, wherein the composition comprises no sulfate based emulsifiers.

7. The personal care composition according to claim 1, wherein the composition is selected from shampoo, scalp cleanser, lotions, creams, veggie wash, different personal care preparation, hair cleanser, shower preparations, shower gels, foam baths, gels, body wash, facial cleanser, face wash, makeup remover, cleansing wipe, sunscreen, and foundation.

8. A nutritional feed for birds comprising glycerol ester mixture comprising at least 30% monoglyceride wherein the glycerol ester mixture is prepared by reacting glycerol with a fatty acid mixture of caprylic acid and capric acid in weight ratio of 30:70 to 70:30; and wherein the glycerol ester mixture protects the birds from LPAI or HPAI when administered with feed.

9. A personal care composition comprising:

a. 0.5 to 10 weight % of glycerol pelargonic ester, wherein the glycerol pelargonic ester comprises at least 30% monoglyceride, and b. one or more excipients selected from anionic, cationic, zwiterrionic, nonionic, and amphoteric surfactants, superfatting agents, stabilizers, biogenic active ingredients, humectants, preservatives, pearlizing agents, dyes, pigments, fragrances, solvents, opacifiers, thickeners, dispersants, protein derivatives, polypeptides, fatty alcohols, odor masking agents, and enzymes.

10. The personal care composition according to claim 9, wherein the glycerol pelargonic ester is effective against microbes.

11. The personal care composition according to claim 10, wherein the microbes are selected from *Staphylococcus aureus, Bacillus subtilis, E. coli, Pseudomonas aeruginosa, Salmonella enteric, Propionebacterium acne, Malassezia furfur, Streptococcus mutans, Lactobacillis acidophilus, Candida albicans*, and *Aspergillus niger.*

12. The personal care composition according to claim 9, wherein the composition comprises no preservative.

13. The personal care composition according to claim 9, wherein the glycerol pelargonic ester emulsifies up to 50% oil by weight.

14. The personal care composition according to claim 9, wherein the composition comprises no sulfate based emulsifiers.

15. The personal care composition according to claim 9, wherein the composition is selected from shampoo, scalp cleanser, lotions, creams, veggie wash, different personal care preparation, hair cleanser, shower preparations, shower gels, foam baths, gels, body wash, facial cleanser, face wash, makeup remover, cleansing wipe, sunscreen, and foundation.

16. The personal care composition according to claim 1, wherein the protein derivatives comprise gelatin, collagen hydrolysates, polypeptides, or a combination thereof.

17. The personal care composition according to claim 9, wherein the protein derivatives comprise gelatin, collagen hydrolysates, polypeptides, or a combination thereof.

* * * * *